(12) United States Patent
Chen et al.

(10) Patent No.: US 7,939,035 B2
(45) Date of Patent: May 10, 2011

(54) SAMPLE PREPARATION DEVICE FOR EXTRACTING DRUG RESIDUE

(75) Inventors: Renyuan Chen, Beijing (CN); Guoqing Wang, Beijing (CN); Feijun Xian, Beijing (CN); Wanli Xing, Beijing (CN); Xianhua Wang, Beijing (CN); Jing Cheng, Beijing (CN)

(73) Assignee: Capitalbio Corporation, Beijing (CN)

( * ) Notice: Subject to any disclaimer, the term of this patent is extended or adjusted under 35 U.S.C. 154(b) by 649 days.

(21) Appl. No.: 11/661,019

(22) PCT Filed: Nov. 22, 2004

(86) PCT No.: PCT/CN2004/001329
§ 371 (c)(1),
(2), (4) Date: Jan. 28, 2008

(87) PCT Pub. No.: WO2006/010300
PCT Pub. Date: Feb. 2, 2006

(65) Prior Publication Data
US 2008/0124251 A1 May 29, 2008

(30) Foreign Application Priority Data

Jul. 30, 2004 (CN) .................... 2004 2 0084611 U

(51) Int. Cl.
*B01D 21/00* (2006.01)
*B01L 99/00* (2010.01)

(52) U.S. Cl. .......... 422/527; 422/99; 422/101; 422/104; 422/500; 422/560

(58) Field of Classification Search .................... 422/99, 422/101, 104
See application file for complete search history.

(56) References Cited

U.S. PATENT DOCUMENTS

| 4,052,518 | A |   | 10/1977 | Borisov et al. |
| 4,389,374 | A | * | 6/1983 | Sutton et al. .................. 422/104 |
| 5,219,839 | A | * | 6/1993 | Bru-Magniez et al. ......... 514/46 |
| 5,399,013 | A | * | 3/1995 | Sawyer ........................ 366/211 |
| 5,459,132 | A | * | 10/1995 | Bru-Magniez et al. ......... 514/46 |
| 5,882,113 | A | * | 3/1999 | Binder .......................... 366/146 |

FOREIGN PATENT DOCUMENTS

| CN | 87214282 U | 7/1988 |
| CN | 2224029 Y | 4/1996 |
| CN | 2350116 Y | 11/1999 |
| CN | 2380922 Y | 5/2000 |
| DE | 43 23 844 A1 | 1/1995 |
| EP | 1 321 756 A1 | 6/2003 |
| GB | 1211942 | 11/1970 |

OTHER PUBLICATIONS

International Search Report mailed Apr. 28, 2005, for PCT Application No. PCT/CN2004/001329, 4 pages.

* cited by examiner

*Primary Examiner* — Sam P Siefke
*Assistant Examiner* — Bryan T Kilpatrick
(74) *Attorney, Agent, or Firm* — Morrison & Foerster LLP

(57) ABSTRACT

The present invention provides a sample preparation device for extracting drug residue. It comprises a case, in which a water bath, a vortex mixer, and a homogenizer are integrated. The case also has on it an integrated control panel for controlling heating temperature of the water bath and homogenization time of the homogenizer.

5 Claims, 4 Drawing Sheets

SAMPLE PREPARATION DEVICE FOR EXTRACTING DRUG RESIDUE

CROSS-REFERENCE TO RELATED APPLICATIONS

This application is a National Phase filing under 35 U.S.C. §371 of International Application No. PCT/CN2004/001329 having an international filing date of Nov. 22, 2004, which claims priority to Chinese Patent Application No. 200420084611.0, filed on Jul. 30, 2004, the contents of each of which are incorporated herein by reference in their entirety.

TECHNICAL FIELD

This application relates generally to the field of sample preparation device. In particular, the invention provides a sample preparation device that can be used to extract drug molecules from a solid sample.

BACKGROUND

Detection of veterinary drug residue in an animal-derived food sample is of great significance for food safety. Sample preparation is the first step during the process of drug residue detection. The aim of sample preparation is to separate out the composition to be analyzed from a given sample, so that the composition can be analyzed. The main purpose of sample preparation is to release the drug residue from the sample, remove the interfering impurities, convert the drug residue to a state that can be analyzed and a concentration that is suitable for analysis, and/or make the drug residue dissolvable in a suitable solvent. The success of sample preparation directly affects the accuracy of drug residue detection.

Sample preparation requires use of devices. At present, there is no device that is specifically designed for detection of drug residue. Instead, many separate apparatuses such as water bath, vortex mixer, homogenizer, and centrifuge have to be used.

However, there are shortcomings for use of the apparatuses:

1) The number of samples that can be processed by a vortex mixer at a given time is very low. Furthermore, because no built-in structures exist for holding the centrifuge tube in the vortex mixer, the operator has to hold the tube(s) against the vortex head for an extended time, leading to hand numbness.

2) There are safety issues associated with use of homogenizers. It is also inconvenient to clean the blade and heads of the homogenizer.

3) Because the apparatuses are not integrated, the efficiency of the operation is very low.

DISCLOSURE OF THE INVENTION

The present invention provides an integrated and convenient device for sample preparation that is useful for extracting drug residue from a sample.

Accordingly, the present invention provides a sample preparation device for extracting drug residue, comprising: a) a case, b) a water bath, a vortex mixer, and a homogenizer, each contained within the case, and c) an integrated control panel on the case for controlling heating temperature of the water bath and homogenization time of the homogenizer.

In one exemplary embodiment, the water bath described herein comprises a container, a built-in centrifuge tube rack inside the container, a heating loop inside the container, and one or more temperature sensors inside the container. The built-in centrifuge tube rack can be double-layered. The vortex mixer comprises one or more vortex heads that are connected to an electricity generator. The vortex mixer may further comprise one or more tube holders that are made of elastic components for tightly holding the centrifuge tubes against the vortex head(s). These elastic tube holders can be made of rubber, metal, or plastic. The homogenizer comprises an electricity generator, blade frame with blade heads, and a sample container. The sample container is connected to the electricity generator via the removable blade frame.

Furthermore, the control panel on the case is connected to each of the following: the heating loop of the water bath, the temperature sensor, the electricity generator for the homogenizer, and the electricity generator for the vortex mixer.

The device of the present invention has the following advantages:

1. The vortex mixer of the device can process multiple samples simultaneously, without the use of hands to hold the tubes;

2. During homogenization of the sample, the operator does not need to stay close to the device. The device thus has improved operation safety;

3. The container for the homogenizer is removable and are therefore easy to wash;

4. The control panel provides a user-friendly interface for operation;

5. The water bath, vortex mixer, and homogenizers are integrated into a single device. The operation is very convenient.

BEST MODE EXAMPLES OF THE PRESENT INVENTION

Figure 1:
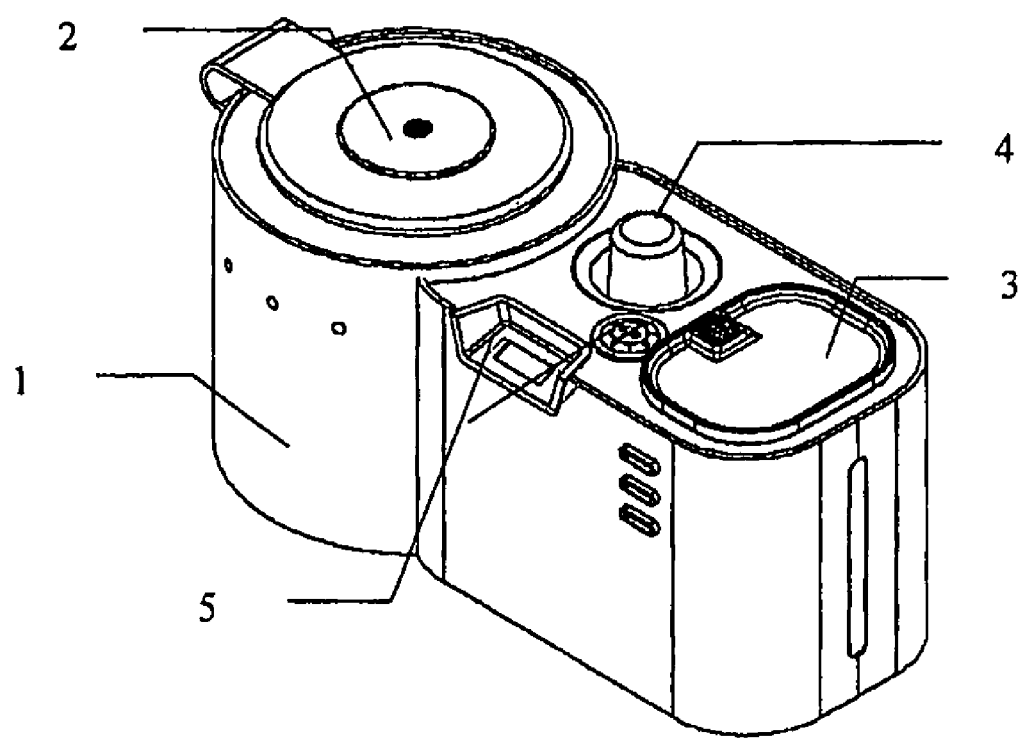
FIG. 1 provides a diagram of one embodiment of the present invention.

As shown in FIG. 1, the sample preparation device for drug residue extraction comprises case 1. Water bath 2, vortex mixer 3, and homogenizer 4 are contained within case 1. An integrated control panel for controlling heating temperature of the water bath and homogenization time of the homogenizer is present on the case.

Figure 2:
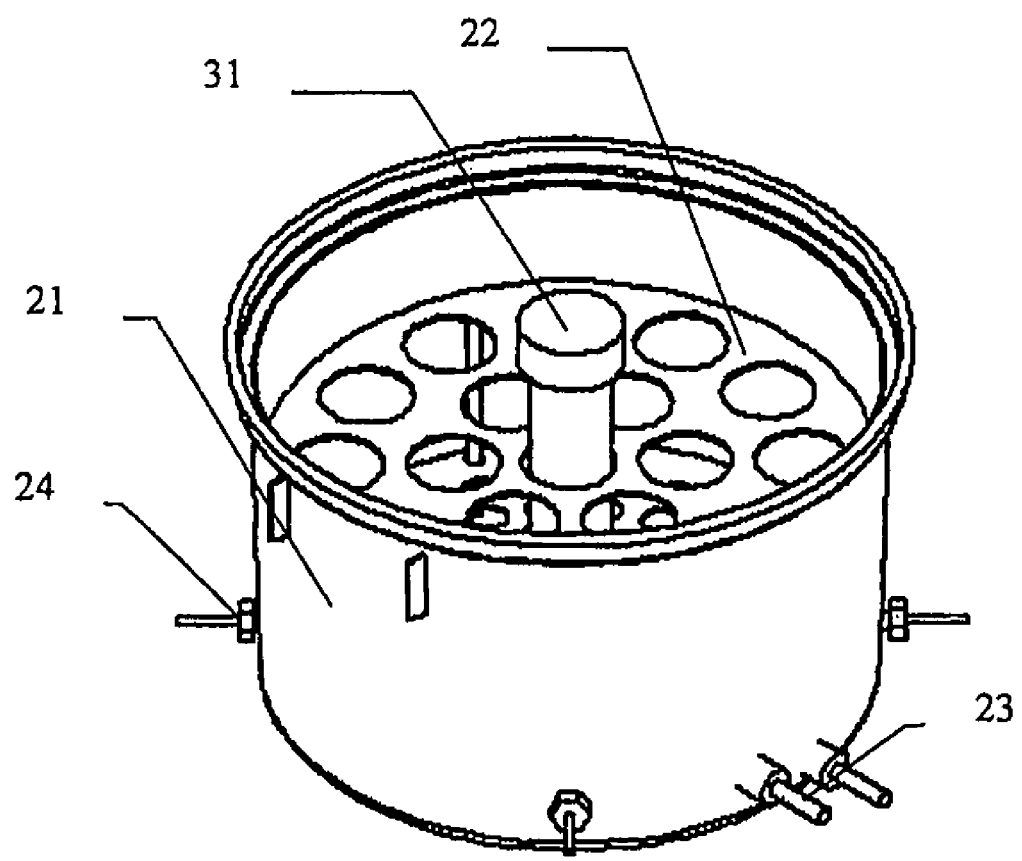
FIG. 2 provides a diagram of a water bath of one embodiment of the present invention.

As shown in FIG. 2, water bath 2 comprises container 21, within which is a built-in centrifuge tube rack 22. In this embodiment, the centrifuge tube rack is double-layered, but of course in certain embodiments the centrifuge tube can also be single-layered if desired. Towards the bottom of the container there is a heating loop 23 and several temperature sensors 24.

Figure 3:
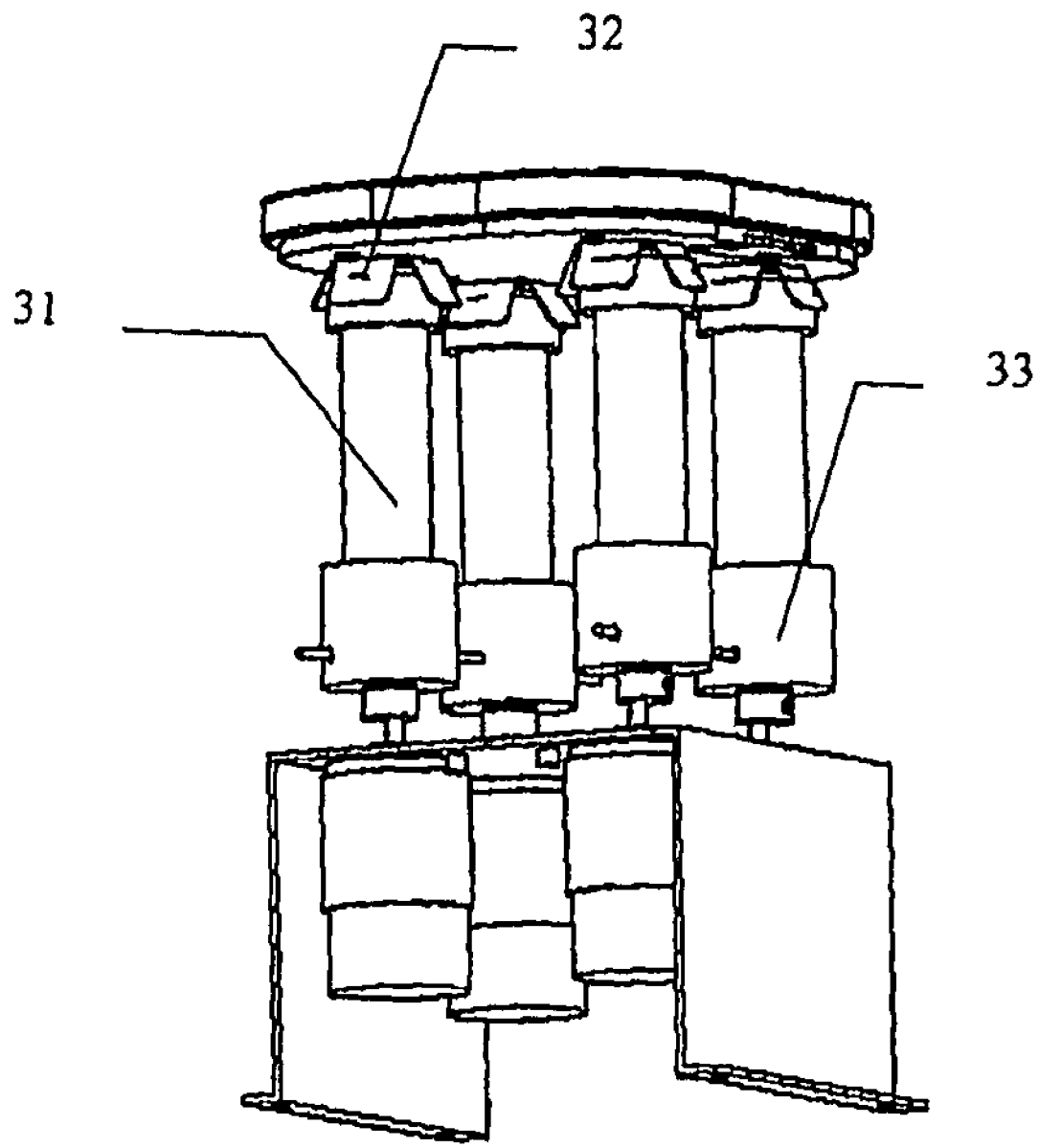
FIG. 3 provides a diagram of a vortex mixer of one embodiment of the present invention.

As shown in FIG. 3, vortex mixer 3 comprises several vortex heads 33 that are connected to an electricity generator. The vortex mixer further comprises tube holders 32 that are made of elastic components for tightly holding the centrifuge tubes against the vortex head. The tube holders are made of rubber, metal, or plastics. In the present example, there are four vortex heads and four tube holders. Four centrifuge tubes can be processed at the same time. The device thus has an increased efficiency.

The upper ends of the centrifuge tubes are connected to the tube holders 32, while the bottom ends of the centrifuge tubes are connected to vortex heads 33. The device thus avoids the use of hands during the vortex operation.

Figure 4:
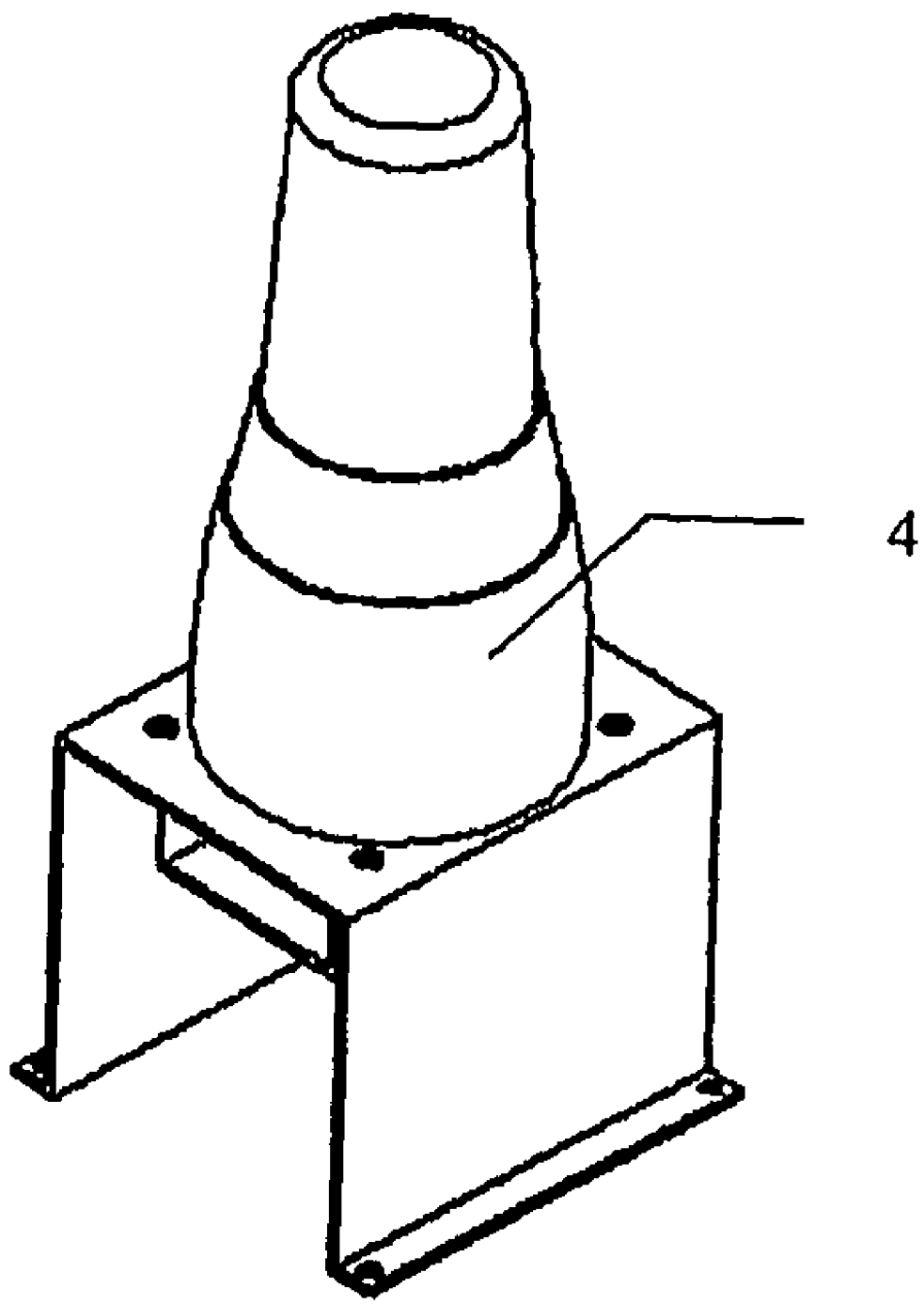
FIG. 4 provides a diagram of a homogenizer of one embodiment of the present invention.

As shown in FIG. 4, homogenizer 4 comprises electricity generator, blade frame with blade heads, and a sample container. The sample container is connected to the electricity generator via the removable blade frame. Homogenizer 4 is used for the homogenization of a tissue sample. Because the operator does not need to operate at close proximity of the device, the device has improved safety in operation. Furthermore, the sample container is removable, and can therefore be easily washed and avoids cross contamination among different samples.

There is also an integrated control panel 11 on case 1. The integrated control panel 11 is connected to each of the following: heating loop 23 of the water bath, temperature sensor 24, electricity generator of the homogenizer, and electricity generator of the vortex mixer. The integrated control panel 11 comprises digital screen and press buttons, and can be used to set the heating temperature of the water bath, homogenization time of the homogenizer, as well as the speed of the vortex mixer.

The operation of the device is further illustrated in the example below for extracting veterinary drug substance from a tissue sample.

1. Use integrated control panel 11 to set homogenization time to 2 minutes. Weigh certain amount of tissue (about 40 grams), place it in the homogenizer 4, and subject the tissue to homogenization.

2. Weigh about 5 grams of homogenate, place it in centrifuge tube 31, add 10 mL extraction solution, close centrifuge tube, and place centrifuge tube 31 in vortex mixer 3. Vortex the tube for 2 minutes.

3. Use integrated control panel 11 to set the heating temperature of water bath 2 to 80° C. After the vortex, the centrifuge tube is placed in water bath 2 and heated for 20 minutes.

4. Subject centrifuge tube 31 to centrifugation on the vortex mixer at the speed of 2000 r/min.

5. Take the supernatant of the centrifuge tube and analyze.

INDUSTRIAL APPLICATION

The device of the present invention is structurally simple and can be used for sample preparation for the detection of drug residue such as streptomycin, sulfonamide, enrofloxacin, and clenbuterol.

What is claimed is:

1. A sample preparation device for extracting drug residue comprising:
   a) a case;
   b) a water bath, a vortex mixer, and a homogenizer, each contained within the case;
   c) an integrated control panel on the case for controlling heating temperature of the water bath and homogenization time of the homogenizer,
   wherein the water bath comprises a container, wherein the container comprises towards its bottom a heating loop and several temperature sensors, wherein the homogenizer comprises an electricity generator, wherein the vortex mixer comprises an electricity generator, and wherein the integrated control panel is connected to the heating loop of the water bath, the temperature sensors, the electricity generator of the homogenizer, and the electricity generator of the vortex mixer.

2. The sample preparation device according to claim 1, further comprising a built-in centrifuge tube rack within the container, wherein the centrifuge tube rack is double-layered.

3. The sample preparation device according to claim 1, wherein the vortex mixer further comprises one or more vortex heads that are connected to the electricity generator of the vortex mixer and one or more tube holders that are made of elastic components for tightly holding centrifuge tubes against the vortex head.

4. The sample preparation device according to claim 3, wherein the tube holder is made of rubber, metal, or plastics.

5. The sample preparation device according to claim 1, wherein the homogenizer further comprises a removable blade frame with a blade head, and a sample container, wherein the sample container is connected to the electricity generator of the homogenizer via the removable blade frame.

\* \* \* \* \*

UNITED STATES PATENT AND TRADEMARK OFFICE
CERTIFICATE OF CORRECTION

PATENT NO.         : 7,939,035 B2
APPLICATION NO.    : 11/661019
DATED              : May 10, 2011
INVENTOR(S)        : Renyuan Chen et al.

It is certified that error appears in the above-identified patent and that said Letters Patent is hereby corrected as shown below:

On the title page, Column 1, Item (73), please add --Tsinghua University--.

Signed and Sealed this
Fifteenth Day of April, 2014

Michelle K. Lee
*Deputy Director of the United States Patent and Trademark Office*